United States Patent
Singh (10) Patent No.: US 11,291,568 B2
(45) Date of Patent: Apr. 5, 2022

(54) RECONFIGURABLE STENT, AND SYSTEMS AND METHODS FOR USE THEREOF

(71) Applicant: C.R. Bard, Inc., Franklin Lakes, NJ (US)

(72) Inventor: Aseem Singh, Tempe, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 83 days.

(21) Appl. No.: 16/640,696

(22) PCT Filed: Aug. 29, 2017

(86) PCT No.: PCT/US2017/049201
§ 371 (c)(1),
(2) Date: Feb. 20, 2020

(87) PCT Pub. No.: WO2019/045695
PCT Pub. Date: Mar. 7, 2019

(65) Prior Publication Data
US 2020/0352756 A1  Nov. 12, 2020

(51) Int. Cl.
*A61F 2/00* (2006.01)
*A61F 2/90* (2013.01)

(52) U.S. Cl.
CPC .............. *A61F 2/90* (2013.01); *A61F 2/0077* (2013.01); *A61F 2002/0086* (2013.01); *A61F 2250/0001* (2013.01); *A61F 2250/0026* (2013.01)

(58) Field of Classification Search
CPC ...... A61F 2/04; A61F 2/82; A61F 2/86; A61F 2/90; A61F 2/93; A61F 2/0077; A61F 2002/0086; A61F 2250/0026; A61F 2250/0001; A61B 2562/028; A61B 2562/0285
See application file for complete search history.

(56) References Cited

U.S. PATENT DOCUMENTS

| | | | |
|---|---|---|---|
| 5,972,029 A | 10/1999 | Fuisz | |
| 6,872,433 B2 | 3/2005 | Seward et al. | |
| 7,097,658 B2 | 8/2006 | Oktay | |
| 7,235,098 B2 | 6/2007 | Palmaz | |
| 2004/0093077 A1* | 5/2004 | White | A61F 2/915 623/1.16 |
| 2008/0009936 A1* | 1/2008 | Kim | A61B 17/11 623/1.15 |
| 2013/0325141 A1* | 12/2013 | Gill | A61F 2/2418 623/23.7 |

* cited by examiner

*Primary Examiner* — Dinah Baria
(74) *Attorney, Agent, or Firm* — Rutan & Tucker LLP (57) ABSTRACT

Provided herein is a system including, in some embodiments, a stent and a catheter. The stent includes a number of filaments arranged to form a tubular body of the stent, a number of microcells forming each filament of the number of filaments, and a port in an end portion of the stent. Each microcell includes a moveable microsurface. The port of the stent may be configured to accept power and control signals for moving the microsurfaces. The catheter may include a cable configured to connect with the port of the stent and provide the power and the control signals for moving the microsurfaces. Moving the microsurfaces may include matching a shape of an anatomical vessel to maintain patency thereof while mitigating stress on the anatomical vessel.

24 Claims, 9 Drawing Sheets

RECONFIGURABLE STENT, AND SYSTEMS AND METHODS FOR USE THEREOF

PRIORITY

This application is a U.S. national stage from International Patent Application No. PCT/US2017/049201, filed Aug. 29, 2017, which is hereby incorporated by reference in its entirety into this application.

BACKGROUND

Stents and related endoluminal devices are used by medical practitioners to treat portions of blood vessels that become so narrow that blood flow through the vessels is restricted. Stents are tubular structures, usually of metal, that can be radially expanded to hold open the narrowed blood vessels (stenoses). Such narrowed blood vessels occur, for example, as a result of arteriosclerosis. Arteriosclerosis can be corrected by angioplasty, but angioplasty can subsequently stimulate excess tissue proliferation that can block newly reopened vessels in a process known as restenosis. Stents are most often used to "prop open" the narrowed blood vessels, but stents can also be used to reinforce collapsed or narrowed tubular structures in the respiratory system, the reproductive system, the hepatic system (e.g., biliary ducts), or any other bodily systems including tubular body structures. However, the amount of force exerted by the stents can (and often does) result in trauma to the tubular structures in which the stents are deployed. Provided herein, in some embodiments, are reconfigurable stents, as well as systems and methods thereof, that address the foregoing.

SUMMARY

Provided herein is a device including, in some embodiments, a tubular body including a lattice structure adapted for an anatomical vessel lumen, with filaments forming at least a portion of the lattice structure, and microcells forming at least a portion of the filaments. Each microcell is configured with a movable microsurface. Combined micromovements of the microsurfaces shape the tubular body. In some embodiments, the shape is optimum for maintaining patency of an anatomical vessel lumen.

In such embodiments, the microcells forming the portion of the filaments are arranged in one or more programmatically addressable rows along respective filaments.

In such embodiments, each microcell includes the microsurface mounted on a torsional hinge over at least a pair of electrodes configured to electrostatically hold in place at least one corner of the microsurface.

In such embodiments, the microsurface is further mounted on a springe-tipped yoke on the torsional hinge, the yoke configured to rotate on the torsional hinge at least +/−12°.

In such embodiments, the microcells are optimized to balance a degree of rotation with a stress placed on rotatable components of the microcells of maintaining patency of an anatomical vessel lumen.

In such embodiments, the lattice structure is a cross-hatched, diamond-celled, or braided lattice structure.

In such embodiments, the lattice structure is a self-expandable lattice structure.

In such embodiments, the self-expandable lattice structure is configured to provide a first, expanded shape through one or more macromovements, and the combined micromovements of the microcells provide a second, non-traumatic optimum shape for maintaining patency of the anatomical vessel lumen.

In such embodiments, each microcell further includes a memory cell configured to store state data for at least one electrode of the pair of electrodes to electrostatically hold in place the at least one corner of the microsurface.

In such embodiments, the device further includes a polymeric casing disposed around the tubular body. The polymeric casing is configured to protect the filaments from corrosion such as corrosion in vivo.

In such embodiments, the polymeric casing is further configured to accept tissue ingrowth. Such tissue ingrowth anchors the device to a wall of an anatomical vessel.

In such embodiments, the device further includes sensors associated with each filament. Each sensor is configured to provide sensor data for moving the microsurfaces.

In such embodiments, the device further includes a port configured to connect with a cable. In some embodiments, the port is in an end portion of the device. The port is configured to accept power and control signals for moving the microsurfaces.

Provided herein is a device including, in some embodiments, a tubular body including a lattice structure adapted for an anatomical vessel lumen, with filaments forming the lattice structure, and microcells forming each filament. Each microcell is configured with a movable microsurface. Combined micromovements of the microsurfaces move the filaments to shape the tubular body. In some embodiments, the shape is optimum for maintaining patency of an anatomical vessel lumen.

In such embodiments, the microcells forming each filament are arranged in one or more programmatically addressable rows along respective filaments.

In such embodiments, each microcell includes the microsurface mounted on a torsional hinge over at least a pair of electrodes configured to electrostatically hold in place at least one corner of the microsurface.

In such embodiments, each microcell further includes a memory cell configured to store state data for at least one electrode of the pair of electrodes to electrostatically hold in place the at least one corner of the microsurface.

In such embodiments, the device further includes a polymeric casing disposed around the tubular body. The polymeric casing is configured to protect the filaments from corrosion such as corrosion in vivo.

In such embodiments, the polymeric casing is further configured to accept tissue ingrowth. Such tissue ingrowth anchors the device to a wall of an anatomical vessel.

In such embodiments, the device further includes sensors associated with each filament. Each sensor is configured to provide sensor data for moving the microsurfaces.

In such embodiments, the device further includes a port configured to connect with a cable. In some embodiments, the port is in an end portion of the device. The port is configured to accept power and control signals for moving the microsurfaces.

Also provided herein is a stent including, in some embodiments, filaments arranged to form a tubular body of the stent, programmatically addressable microcells forming each filament, and movable microsurfaces. Each microsurface is configured to tilt a first microsurface corner toward a blood vessel wall and a second microsurface corner away from the blood vessel wall in vivo. The microcells are configured to move these microsurfaces to match a blood vessel wall, thereby maintaining patency while mitigating stress on the blood vessel wall.

In such embodiments, each microsurface is mounted on a torsional hinge over at least a pair of electrodes configured to electrostatically hold in place at least one corner of the microsurface.

In such embodiments, the stent further includes a polymeric casing disposed about the tubular body of the stent. The polymeric casing is configured to protect the filaments from corrosion in vivo and accept tissue ingrowth for anchoring the stent to a blood vessel wall.

In such embodiments, the stent further includes sensors disposed along each filament. Each sensor is configured to provide sensor data for moving the microsurfaces.

In such embodiments, the stent further includes a port configured to connect with a cable. In some embodiments, the port is in an end portion of the stent. The port is configured to accept power and control signals for moving the microsurfaces.

Also provided herein is a system including, in some embodiments, a stent and a catheter. The stent includes filaments arranged to form at least a portion of a tubular body of the stent, microcells forming at least a portion of the filaments, and a port. Each microcell includes a moveable microsurface. The port is configured to accept power and control signals for moving the microsurfaces. The catheter includes a cable configured to connect with the port of the stent and provide the power and the control signals for moving the microsurfaces. Moving the microsurfaces includes matching a shape of a vessel. In some embodiments, the shape is optimum for maintaining patency of the vessel while mitigating stress on the vessel.

In such embodiments, the stent further includes a polymeric casing disposed around the tubular body. The polymeric casing is configured to protect the filaments from corrosion in vivo and accept tissue ingrowth for anchoring the stent to a wall of a vessel.

In such embodiments, the port is a magnetic port configured to facilitate reconnecting the cable with the port when the stent is disposed in vivo.

In such embodiments, the stent further includes sensors disposed along each filament. Each sensor is configured to provide sensor data over the cable for moving the microsurfaces.

In such embodiments, the catheter further includes a microcontroller including a shape-determining algorithm in memory configured for matching a shape of a vessel from the sensor data. In some embodiments, the shape is optimum for maintaining patency of a vessel while mitigating stress on the vessel.

In such embodiments, each microsurface is configured to tilt a first microsurface corner toward a wall of a vessel and a second microsurface corner away from the wall of the vessel in vivo.

In such embodiments, each microsurface is mounted on a torsional hinge over at least a pair of electrodes configured to electrostatically hold in place at least one corner of the microsurface.

In such embodiments, each microsurface is further mounted on a springe-tipped yoke on the torsional hinge, the yoke configured to rotate on the torsional hinge at least +/−12°.

In such embodiments, the microcells are optimized to balance a degree of rotation with a stress placed on rotatable components of the microcells while maintaining patency of a vessel and mitigating stress on the vessel.

In such embodiments, the tubular body of the stent includes a lattice structure, the lattice structure being a cross-hatched, diamond-celled, or braided lattice structure.

In such embodiments, the lattice structure is a self-expandable lattice structure.

In such embodiments, the self-expandable lattice structure is configured to provide a first, expanded shape through one or more macromovements, and moving the microsurfaces includes one or more micromovements to provide a second, non-traumatic matching shape for maintaining patency of the vessel while mitigating stress on the vessel.

Also provided herein is a system including, in some embodiments, a stent and a catheter. The stent includes filaments arranged to form a tubular body of the stent, microcells forming each filament, and a port. Each microcell includes a moveable microsurface. The port is configured to accept power and control signals for moving the microsurfaces. The catheter includes a cable configured to connect with the port of the stent and provide the power and the control signals for moving the microsurfaces. Moving the microsurfaces includes matching a shape of a vessel. In some embodiments, the shape is optimum for maintaining patency of the vessel while mitigating stress on the vessel.

In such embodiments, the stent further includes a polymeric casing disposed around the tubular body. The polymeric casing is configured to protect the filaments from corrosion in vivo and accept tissue ingrowth for anchoring the stent to a wall of a vessel.

In such embodiments, the port is a magnetic port configured to facilitate reconnecting the cable with the port when the stent is disposed in vivo.

In such embodiments, the stent further includes sensors disposed along each filament. Each sensor is configured to provide sensor data over the cable for moving the microsurfaces.

In such embodiments, the catheter further includes a microcontroller including a shape-determining algorithm in memory configured for matching a shape of a vessel from the sensor data. In some embodiments, the shape is optimum for maintaining patency of a vessel while mitigating stress on the vessel.

In such embodiments, each microsurface is configured to tilt a first microsurface corner toward a wall of a vessel and a second microsurface corner away from the wall of the vessel in vivo.

In such embodiments, each microsurface is mounted on a torsional hinge over at least a pair of electrodes configured to electrostatically hold in place at least one corner of the microsurface.

These and other features of the concepts provided herein may be better understood with reference to the drawings, description, and appended claims.

DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

With respect to "proximal," a "proximal portion" or a "proximal end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Stents and related endoluminal devices are used by medical practitioners to treat portions of blood vessels that become so narrow that blood flow through the vessels is restricted. Stents are tubular structures including tubular bodies, usually of metal, that can be radially expanded to hold open the narrowed blood vessels (stenoses). Such narrowed blood vessels occur, for example, as a result of arteriosclerosis. Arteriosclerosis can be corrected by angioplasty, but angioplasty can subsequently stimulate excess tissue proliferation that can block newly reopened vessels in a process known as restenosis. Stents are most often used to "prop open" the narrowed blood vessels, but stents can also be used to reinforce collapsed or narrowed tubular structures in the respiratory system, the reproductive system, the hepatic system (e.g., biliary ducts), or any other bodily systems including tubular body structures. However, the amount of force exerted by the stents can (and often does) result in trauma to the tubular structures in which the stents are deployed. Provided herein, in some embodiments, are reconfigurable stents, as well as systems and methods thereof, that address the foregoing.

Figure 1A:
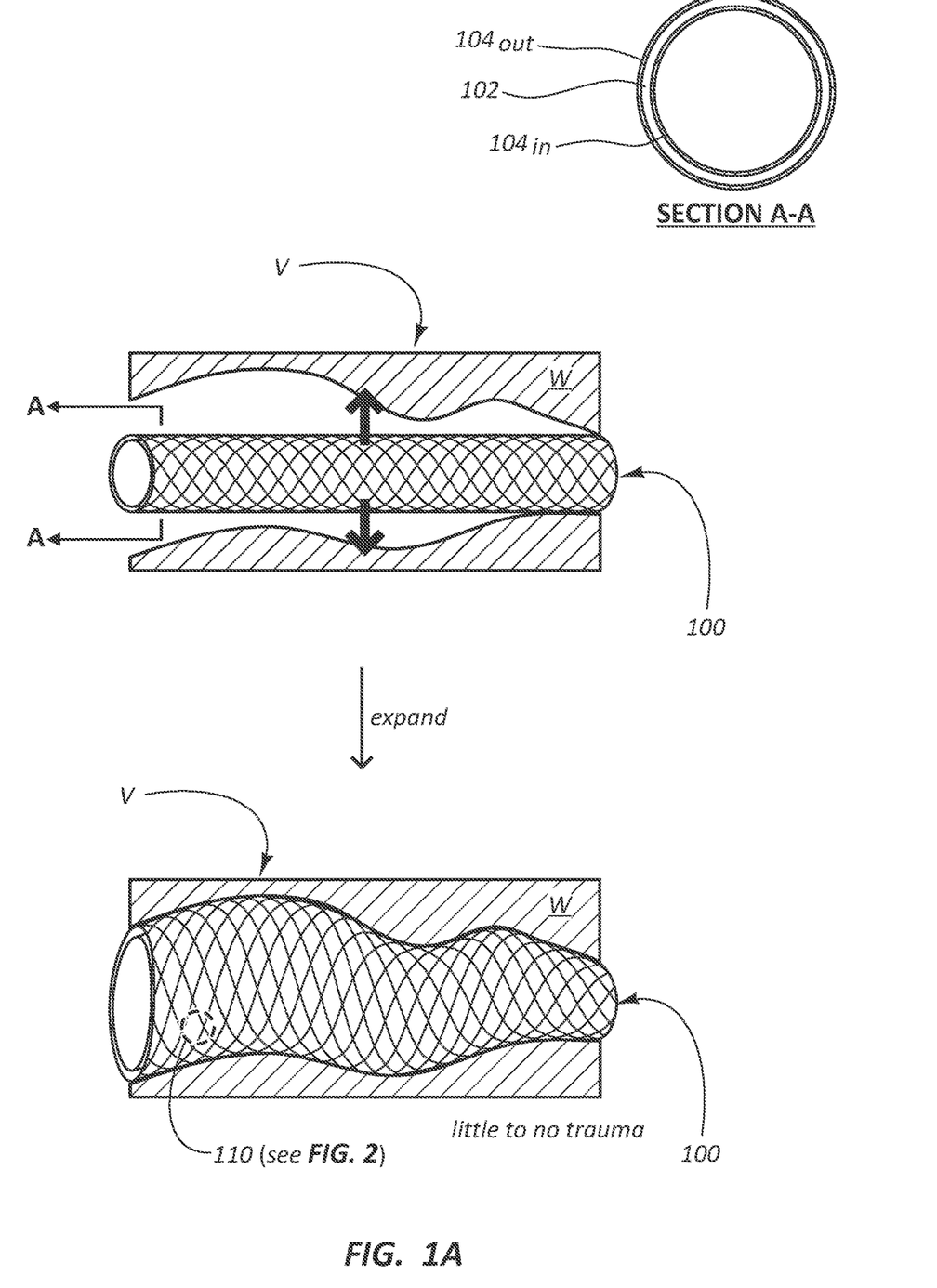
FIG. 1A provides a schematic illustrating a reconfigurable stent in accordance with some embodiments.

FIG. 1A provides a schematic illustrating a reconfigurable stent 100 in accordance with some embodiments.

As shown in FIG. 1A, the reconfigurable stent 100 includes a tubular body sized to fit within a lumen of a vessel. The reconfigurable stent 100 is further sized to interface with a deployment device (e.g., catheter 500 of FIG. 5) for traversing anatomy and deploying the reconfigurable stent 100. Because the reconfigurable stent 100 can be used in any system including tubular body structures (e.g., the vascular system, the respiratory system, the reproductive system, the hepatic system, etc.), the reconfigurable stent 100 can be sized in a number of different diameters and lengths as needed for the system or application.

Figure 1B:
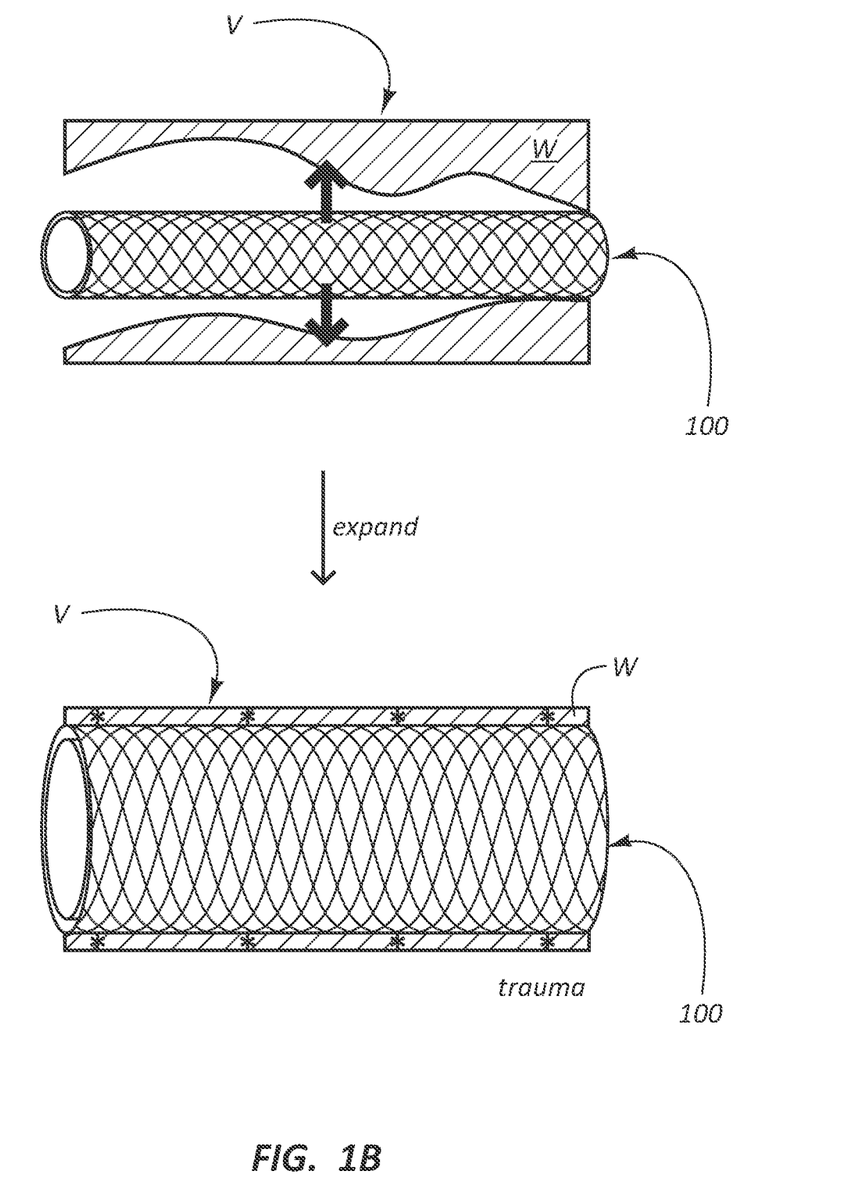
FIG. 1B provides a schematic illustrating trauma resulting from an existing stent being deployed in a tubular structure.

For example, FIG. 1A shows the reconfigurable stent 100 initially deployed in a blood vessel V of the vascular system in an unexpanded state such as after deployment of an angioplasty balloon. The reconfigurable stent 100 can be subsequently expanded into an expanded state against wall W of the blood vessel V and configured to match the shape of the blood vessel V. By matching the shape of the blood vessel V, the reconfigurable stent 100 produces little to no trauma on the wall W of the blood vessel V while maintaining patency of the blood vessel V. This is a marked improvement over existing stents as shown in FIG. 1B, which can, and often do, cause trauma to the vessels in which the stents are deployed. As such, the reconfigurable stent 100 is configured to maintain patency while mitigating stress on vessel walls such as blood vessel walls.

The reconfigurable stent 100 includes a number of filaments such as filament 110, wherein the filaments are arranged into a lattice structure or segmented structure. While the lattice structure of the reconfigurable stent 100 is shown as a cross-hatched, diamond-celled, or braided lattice structure, the lattice structure can vary as needed for the system or application. In some embodiments, for example, the lattice structure of the reconfigurable stent 100 is a self-expandable lattice structure, of which, there are many examples. Such a self-expandable lattice structure is useful for expanding the reconfigurable stent 100 by one or more macromovements into a first, expanded shape to interface with a lumen of a vessel. Subsequently, a number of micromovements can provide the reconfigurable stent 100 with a second, non-traumatic optimum shape for maintaining patency of the vessel in which the reconfigurable stent 100 is disposed. However, the lattice structure of the reconfigurable stent 100 need not be a self-expandable lattice structure to make use of both macro- and micromovements to provide the reconfigurable stent 100 with the optimum shape for maintaining patency of the vessel in which the reconfigurable stent 100 is disposed. In some embodiments, the reconfigurable stent 100 is configured to assume and retain (via reconfiguration) the optimum shape for maintaining patency of the vessel in which the reconfigurable stent 100 is disposed merely through these micromovements.

As further shown in FIG. 1A, the tubular body of the reconfigurable stent 100 can, in some embodiments, be encased with a casing to protect the filaments from corrosion in vivo. This is shown in FIG. 1A by Section A-A, in which the lattice structure is represented by layer 102, and the casing is represented by the layers $104_{in}$ and $104_{out}$. The casing can be a polymeric casing including, but not limited to, polytetrafluoroethylene ("PTFE") such as expanded PTFE ("ePTFE"), which ePTFE is configured to accept tissue ingrowth for anchoring the reconfigurable stent 100 to a wall of a vessel. Indeed, PTFE has proven advantageous as a material from which to fabricate blood vessel grafts or prostheses used to replace damaged or diseased blood vessels. This is because PTFE is an extremely biocompatible material causing little or no immunogenic reaction in vivo. This is also because ePTFE is porous due to fibrils of PTFE separated by nodes. Living cells can colonize the nodes of a casing of ePTFE allowing a reconfigurable stent 100 encased with an ePTFE casing to become a permanent part of a living body.

Figure 2:
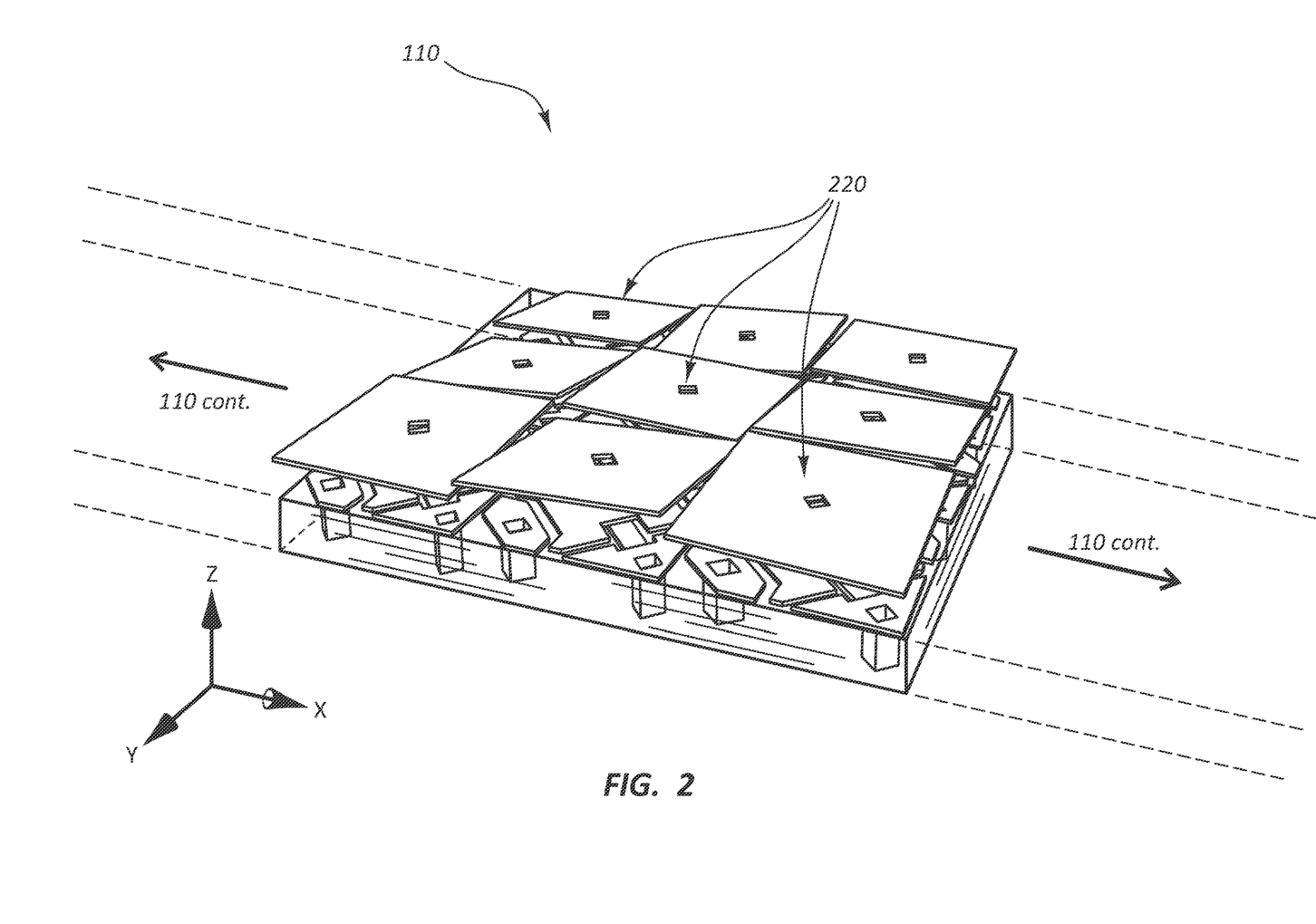
FIG. 2 provides a schematic illustrating a number of microcells forming a portion of a filament of a reconfigurable stent in accordance with some embodiments.

FIG. 2 provides a schematic illustrating a number of microcells 220 forming a portion of a filament 110 of a reconfigurable stent 100 in accordance with some embodiments.

Firstly, the portion of the filament 110 is merely an example of a portion of a filament of any of the number of filaments in the lattice structure of the reconfigurable stent 100. Secondly, while nine microcells 220 are shown in FIG. 2, these are merely an example of the number of microcells 220 forming the portion of the filament 110 of the reconfigurable stent 100 indicated in FIG. 1A. The reconfigurable stent 100 can include millions or more microcells (e.g., $10^6$ microcells or more per filament), each microcell measuring, at most, tens of μm across. As shown, the portion of the filament 110 can be longitudinally extended with any number of additional microcells 220 along the positive or negative direction (or both) of the x-coordinate of the coordinate system of FIG. 2. The portion of the filament 110 can also be transversely extended with any number of additional microcells 220 (or transversely contracted by one or two microcells) along the positive or negative direction (or both) of the y-coordinate of the coordinate system of FIG. 2. That is, neither the portion of the filament 110, nor any portion of the number of filaments the portion of the filament 110 represents, is limited to a width of three microcells. The number of microcells 220 forming each filament can be arranged in one or more longitudinally or transversely oriented rows along their respective filaments. These rows are programmatically addressable for individually addressing the microcells.

As further shown in FIG. 2, each microcell of the number of microcells 220 includes a microsurface 332 (see FIG. 3A) independently movable in any direction of at least two different directions. It is the ability of each microsurface 332 to move in one direction or another through one or more micromovements that enables the reconfigurable stent 100 to adopt an optimum shape for maintaining patency of a vessel and to maintain the optimum shape by subsequent reconfiguration of the reconfigurable stent 100. Indeed, combined micromovements move the filaments to provide the optimum shape for maintaining the patency of the vessel.

Figure 3A:
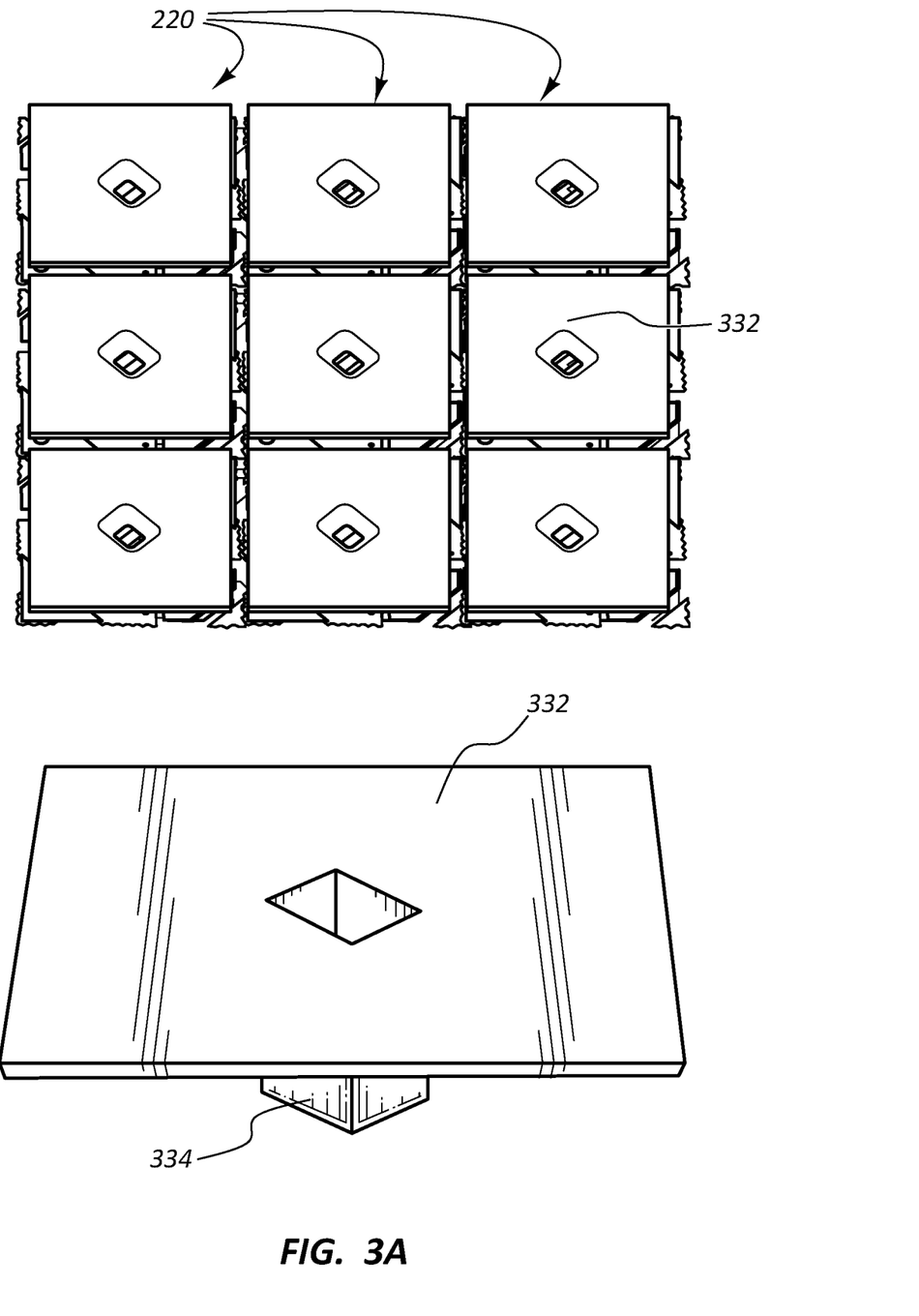
FIG. 3A provides an image from above a number of microcells, as well as a complementary schematic illustrating a portion of a microcell, in accordance with some embodiments.
Figure 3B:
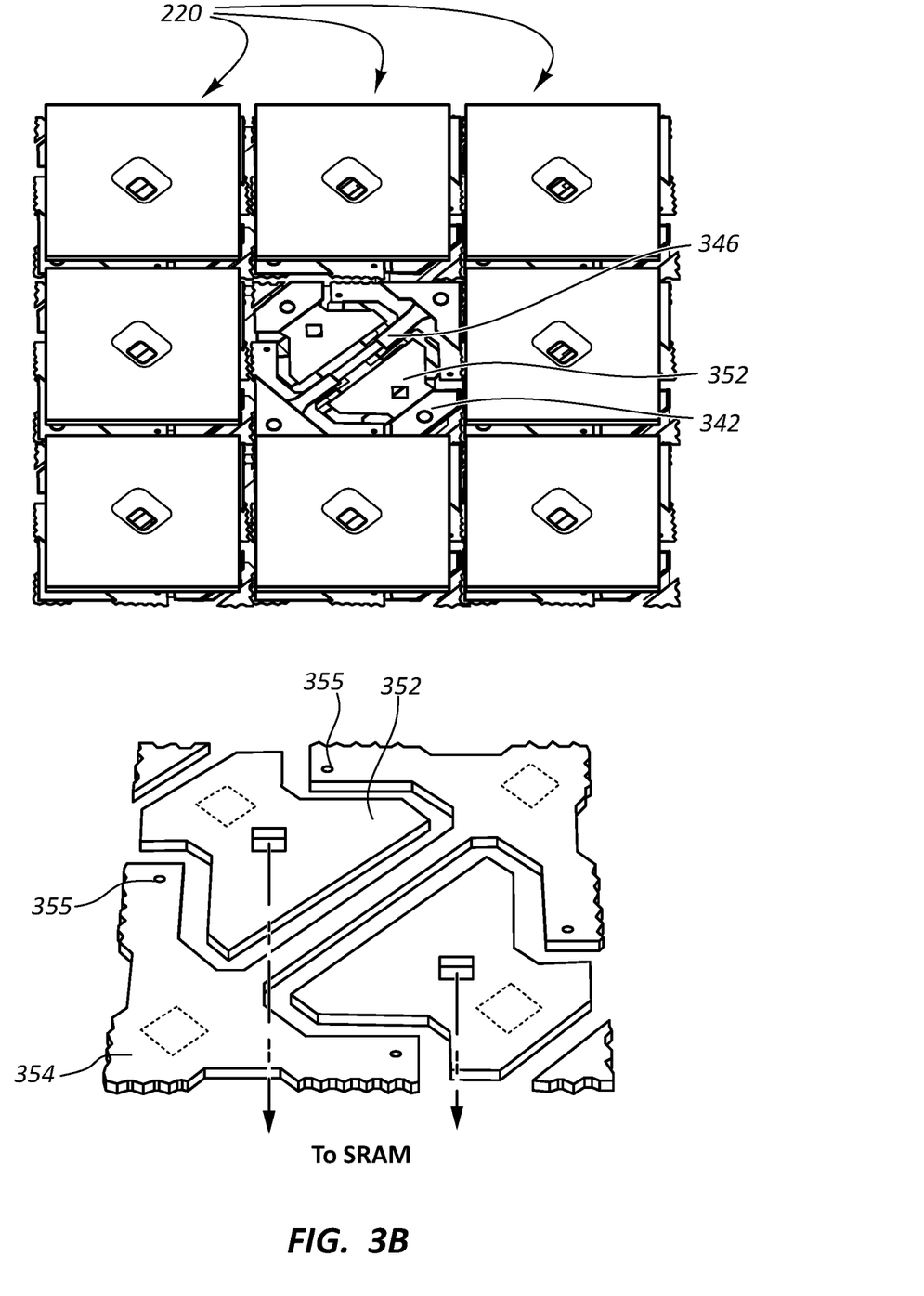
FIG. 3B provides an image from above a number of microcells including a partially disassembled microcell, as well as a complementary schematic illustrating a portion of a microcell, in accordance with some embodiments.
Figure 3C:
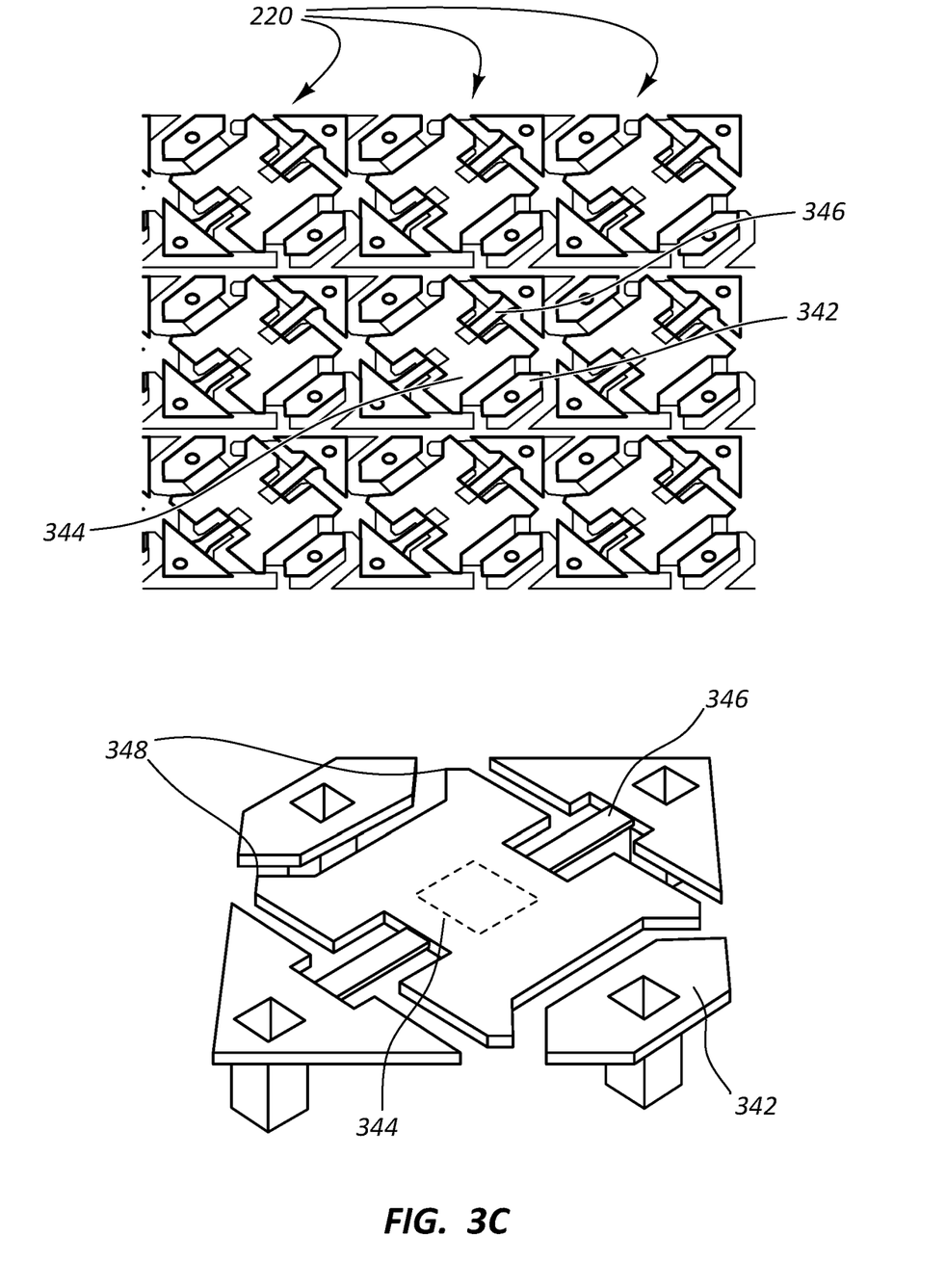
FIG. 3C provides an image from above a number of partially disassembled microcells, as well as a complementary schematic illustrating a portion of a microcell, in accordance with some embodiments.

FIGS. 3A-3C provide images and schematics illustrating a number of microcells 220 of a reconfigurable stent 100 in accordance with some embodiments. FIG. 3A provides an image from above a number of microcells, as well as a complementary schematic illustrating a portion of a microcell; FIG. 3B provides an image from above a number of microcells including a partially disassembled microcell, as well as a complementary schematic illustrating a portion of a microcell; and FIG. 3B provides an image from above a number of partially disassembled microcells, as well as a complementary schematic illustrating a portion of a microcell.

As shown among FIGS. 3A-3C and 4, each microcell of the number of microcells 220 includes a microsurface 332 including a post 334 configured for mounting the microsurface 332 on a yoke 344 with a torsional hinge 346. Each microcell further includes at least a pair of electrodes configured to electrostatically hold in place at least one corner of the microsurface 332. For example, a corner of the microsurface 332 (e.g., the left corner of the microsurface 332 of FIG. 4 including the reference line and numeral 332 for the microsurface 332) can be electrostatically held in place by an underlying electrode 342 when the yoke 344 underlying the microsurface 332 is rotated (e.g., up to +/−12° or more, such as +/−17°) by the torsional hinge 346 toward the electrode 342. As such, each microsurface 332 of the number of microcells 220 is configured to tilt its first corner toward a wall of a vessel and its second corner (e.g., the left corner of the microsurface 332 of FIG. 4) away from the wall of the vessel when disposed in vivo.

Figure 4:
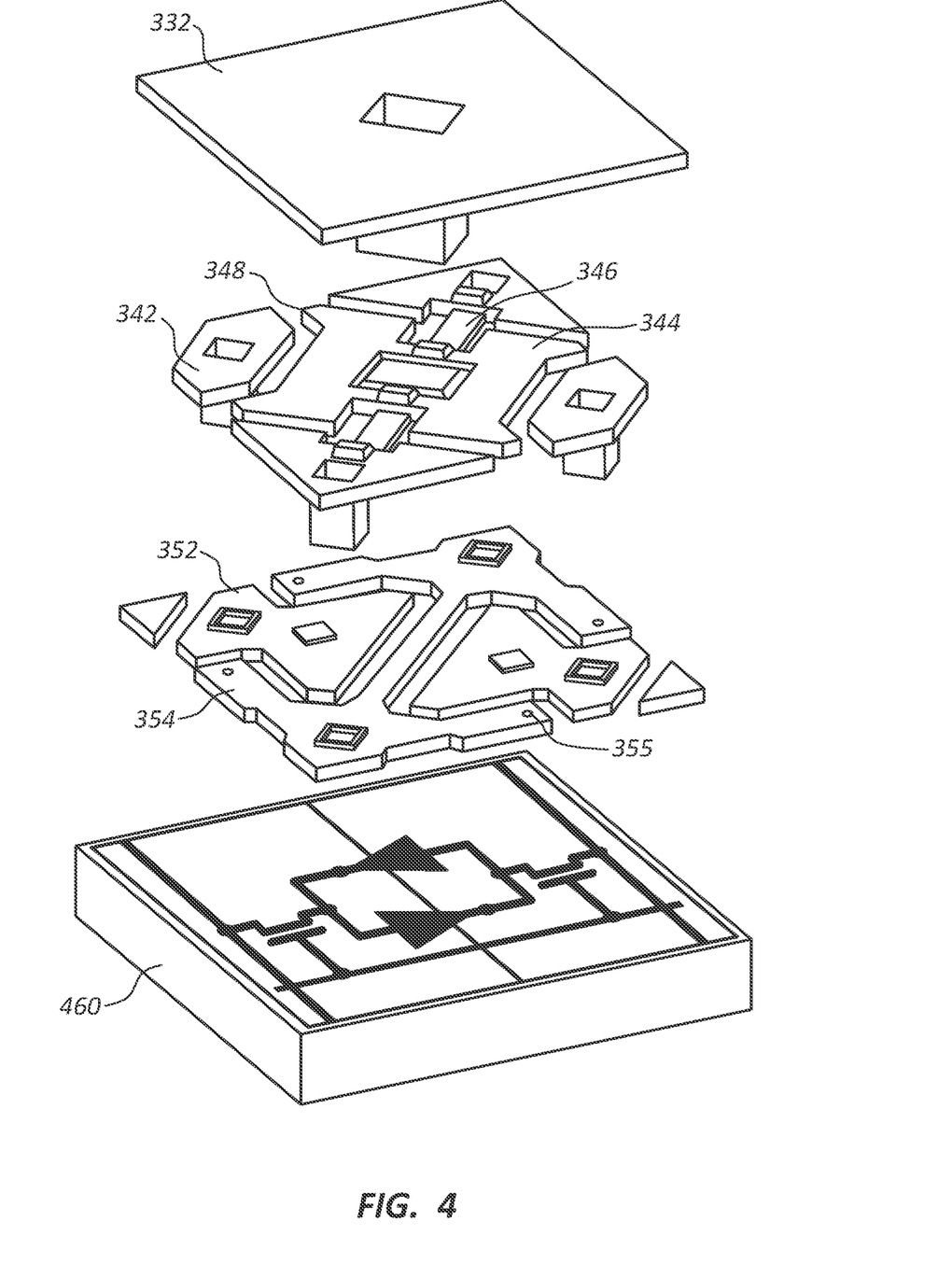
FIG. 4 provides a schematic illustrating an exploded view of a single microcell of a reconfigurable stent in accordance with some embodiments.

The axle of the torsional hinge 346 is fixed at both ends at yoke posts of the yoke 344, and the torsional hinge 346 twists in the middle (e.g., where the post 334 of the microsurface 332 is mounted on the yoke 344). Because of the small scale of the microcells (e.g., just tens of μm across), hinge fatigue is not a problem with the torsional hinge 346. This allows for unlimited reconfiguration of the reconfigurable stent 100 to first assume and retain the desired shape, such as the optimum shape for maintaining patency of the vessel.

A stop 354 extends from one corner of a microcell to a diagonally opposing corner of the microcell, and the stop 354 includes stops or landing sites 355 at termini of the stop 354 configured to oppose the yoke 344 and prevent over rotation. Yoke tips 348 (optionally spring-tipped yoke tips 348) contact the landing sites 355 preventing over-rotation.

In some embodiments, such mechanical microcell parts comprise aluminum or other bio-insensitive materials.

The degree of rotation (e.g., up to +/−12° or more, such as +/−17°) of the microsurface 332 depends upon a distance between a corner of the microsurface 332 and the underlying electrode 342, a distance between a set of the yoke tips 348 on the yoke 344 and the underlying landing sites 355, or a combination of these. An increase in one or more of the foregoing distances configures the microsurface 332 for a greater degree of rotation, and a decrease in one or more of the foregoing distances configures the microsurface 332 for a lesser degree of rotation. In some embodiments, for example, each of the number of microsurfaces is configured to rotate at least +/−1°, +/−5°, +/−10°, +/−12°, +/−15°, +/−17°, +/−20°, +/−25°, +/−30°, +/−35°, or +/−45°, optionally in increments thereof such as by one-digit increments. In some embodiments, for example, each of the number of microsurfaces is configured to rotate no more than +/−45°, +/−35°, +/−30°, +/−25°, +/−20°, +/−17°, +/−15°, +/−12°, +/−10°, +/−5°, or +/−1°, optionally in increments thereof such as by one-digit increments. As such, in some embodiments, each of the number of microsurfaces is configured to rotate between +/−1° and +/−45°, including between +/−5° and +/−25°, such as between +/−10° and +/−25°, and, for example, between +/−12° and +/−17°. Microsurfaces with a greater degree of rotation can be used to push a wall of a vessel out from an initial position or shape (e.g., the first, expanded shape set forth above) of the reconfigurable stent 100; however, the greater degree of rotation can put greater stress on components of the microcells. Microcells can be optimized as needed to balance the degree of rotation with the stress on their components.

As further shown in at least FIGS. 3C and 4, the layer of the number of microcells 220 including the stop 354 further includes at least a pair of address pads 352 in electrical communication with overlying electrodes via posts of the overlying electrodes. Again, each microcell of the number of microcells 220 includes at least a pair of electrodes, which electrodes are in a one-to-one correspondence with the address pads 352. As set forth above, the number of microcells 220 forming each filament can be arranged in one or more longitudinally or transversely oriented rows along their respective filaments, which rows are programmatically addressable for individually addressing the microcells such as through the address pads 352.

Each microcell of the number of microcells 220 further includes a memory cell 460 (e.g., static random-access memory ["SRAM"] built with complementary metal-oxide semiconductor ["CMOS"] technology) configured to store state data for at least one electrode 342 of the pair of electrodes (through a corresponding address pad) to electrostatically hold in place at least one corner of the microsurface 332.

In operation, the pair of electrodes for each microcell controls the position of the microsurface 332 by electrostatic attraction. The pair of electrodes includes at least one electrode 342 on each side of the torsional hinge 346, with the at least one electrode 342 positioned to act on the yoke 344, the microsurface 332, or both the yoke 344 and the microsurface 332. A majority of the time, equal bias charges are simultaneously applied to both sides of the pair of electrodes. Instead of the microsurface 332 flipping to a central position, the equal bias charges actually hold the microsurface 332 in its current position.

To move the microsurface 332 of a microcell, a microcell controller (see FIG. 6) first loads the state into the memory cell 460 located at the bottommost layer of the microcell. The memory cell, in turn, is electrically connected to the pair of electrodes through the address pads 352. The state loaded into the memory cell 460 is loaded into two complimentary memory elements. That is, if one memory element is a logical '1' the other memory element is a logical '0' (and vice versa). The state loaded into the memory cell 460 plays a part in moving the microsurface 332; however, loading the memory cell 460 does not automatically move the microsurface 332. In order for the state loaded into the memory cell 460 to be transferred into a micromovement of the microsurface 332, the microcell must receive a reset or clocking pulse. The reset or clocking pulse momentarily releases the microsurface 332 enabling it to move based on the state loaded into the memory cell 460. Movement of the microsurface 332 into the + or − degree state is highly repeatable due to landing sites 355 of the stop 354 against the yoke tips 348. The reset or clocking pulse allows the memory cells of any set of the number of microcells 220 on one more filaments of the reconfigurable stent 100 to be pre-loaded for subsequent and simultaneous combined micromovements to move the one or more filaments with the reset or clocking pulse.

Movement of a filament is created by programming an on/off duty cycle for one or more microcells in the filament. The one or more microcells can be multiplexed to create an overall movement of the filament. In addition, the microcells in two or more filaments can be multiplexed to create movement in the two or more filaments. For example, the microcells of the two or more filaments can be multiplexed to move the filaments into the first, expanded shape to interface with the lumen of the vessel. A number of micromovements can be made to provide the reconfigurable stent 100 with the second, non-traumatic optimum shape for maintaining patency of the vessel in which the reconfigurable stent 100 is disposed.

Reconfigurable stents such as the reconfigurable stent 100 can be manually controlled in real-time, or advanced imaging techniques (e.g., fluoroscopy) can be used as an aid to determine a best possible shape and orientation of the reconfigurable stents.

Figure 5:
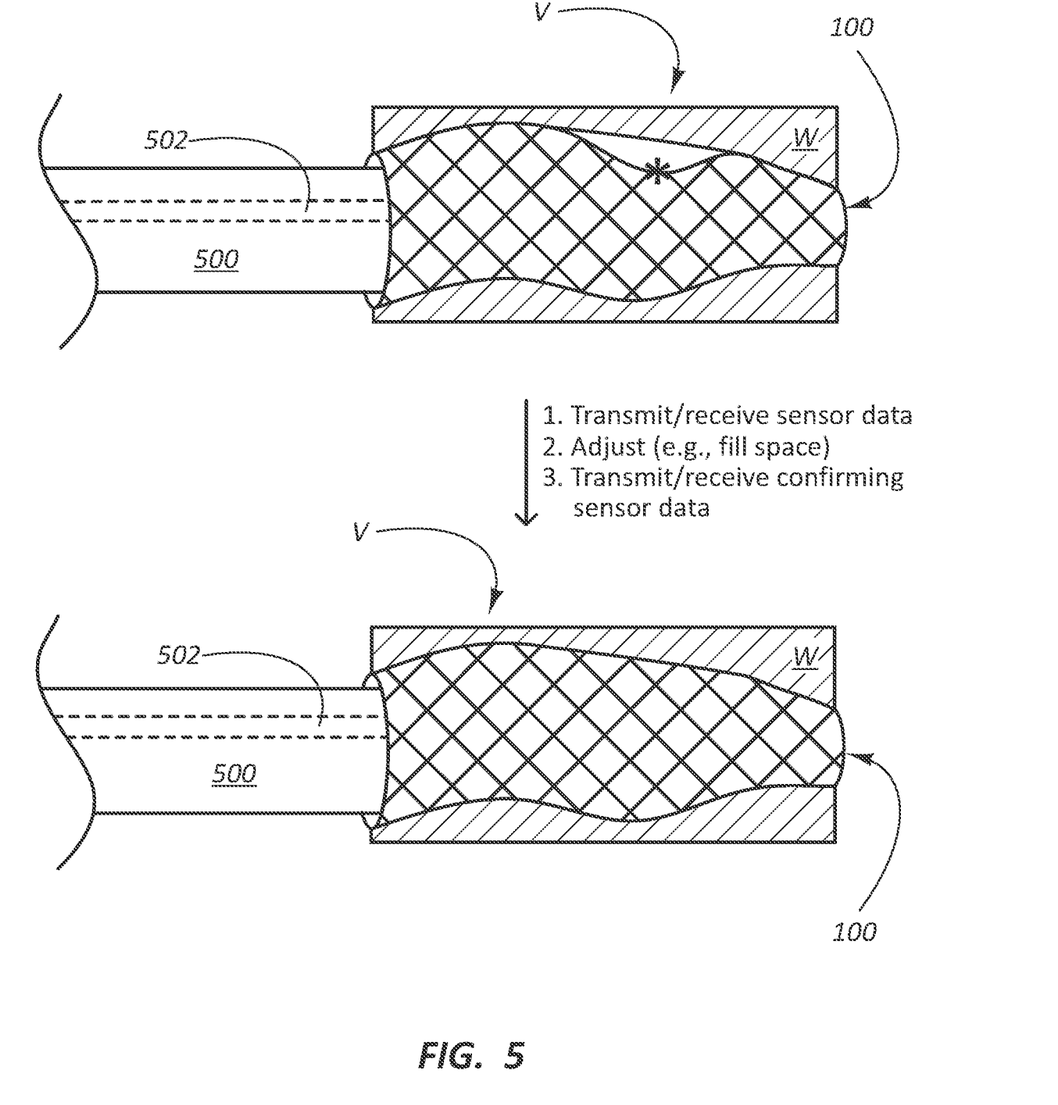
FIG. 5 provides a schematic illustrating a reconfigurable stent engaged with a catheter for reconfiguring the stent in accordance with some embodiments.

FIG. 5 provides a schematic illustrating a reconfigurable stent 100 engaged with a catheter 500 for reconfiguring the reconfigurable stent 100 in accordance with some embodiments.

As shown in FIG. 5, a system includes the reconfigurable stent 100 and the catheter 500. The reconfigurable stent 100 can further include a port (see port 670 of FIG. 6) within an end portion or at an end of the reconfigurable stent 100. The port of the reconfigurable stent 100 can be configured to accept power, control signals, or both power and control signals for moving the microsurfaces of the number of microcells 220. The catheter can include a catheter cable 502 disposed within the catheter 500 configured to connect with the port of the reconfigurable stent 100 and provide the power, the control signals, or a combination of these for moving the microsurfaces of the number of microcells 220. The port of the reconfigurable stent 100 can be a magnetic port, and the catheter cable 502 can have a complimentary magnetic end configured to facilitate reconnecting the catheter cable 502 with the port for subsequent reconfiguration of the reconfigurable stent 100 when the reconfigurable stent 100 is disposed in vivo.

As further shown in FIG. 5, the reconfigurable stent 100 can further include a number of sensors associated with or otherwise disposed along each filament of the reconfigurable stent 100. One such sensor is indicated by the asterisk ('*') in FIG. 5. Each sensor can be configured to provide sensor data over the catheter cable 502 for subsequently moving the microsurfaces of the number of microcells 220. The catheter 502 can further include a microcontroller including a shape-determining algorithm in memory configured for matching a shape of a vessel from the sensor data in order to maintain vessel patency while mitigating stress on the vessel. Sensor data communicated to the shape-determining algorithm can be used for advanced adherence, as well as less traumatic interaction with the vessel.

The catheter 500 can be configured to slide up a low-profile cable rail with the reconfigurable stent 100 for deployment of the reconfigurable stent 100. Once the reconfigurable stent 100 is deployed in a vessel, the system, which includes the catheter cable 502 of the catheter 500 connected to the port of the reconfigurable stent 100, can be configured to match the shape of the reconfigurable stent 100 to the vessel. The system can be further configured to detach the catheter 500 from the reconfigurable stent 100 after the shape of the reconfigurable stent 100 is matched to the vessel. The catheter 500 can be subsequently be removed and the reconfigurable stent can be left in vivo.

Figure 6:
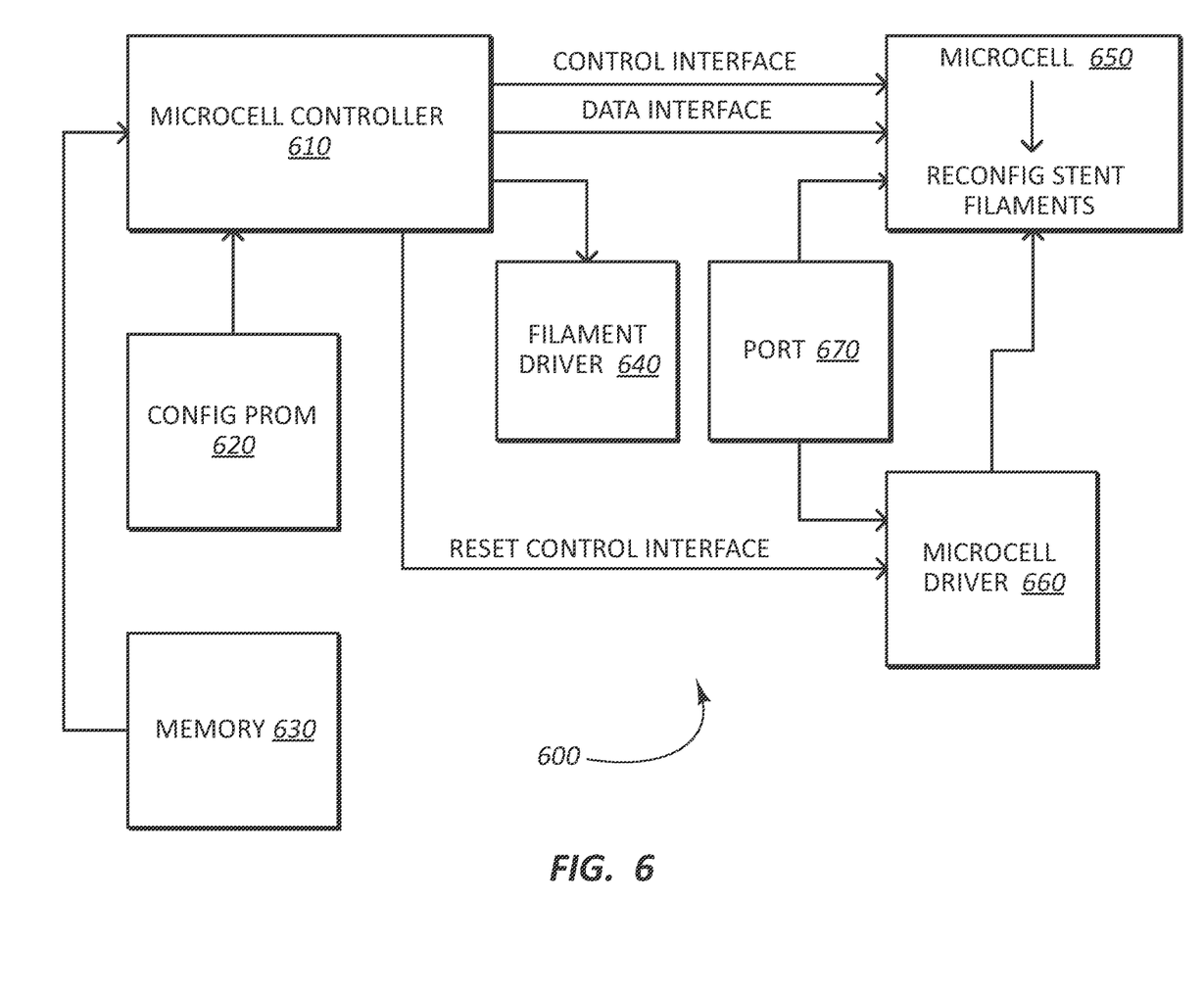
FIG. 6 provides a schematic illustrating a system architecture of a reconfigurable stent in accordance with some embodiments.

FIG. 6 provides a schematic illustrating a system architecture of a reconfigurable stent 100 in accordance with some embodiments.

As shown in FIG. 6, the system architecture of the reconfigurable stent 100 can include a microcell controller 610, firmware 620 for the reconfigurable stent 100, memory 630, filament driver 640, microcell 650 of the number of microcells 220, a microcell driver 660, and a port 670, which components can be connected as shown. For example, the microcell controller 610 can be connected to the microcell 650 and configured to provide data and control signals for configuring the microcell 650. The microcell controller 610 can also be connected to the microcell driver 660, which, in turn, can be connected to the microcell 650 and configured to provide reset or clocking pulses to momentarily release the microsurface 332 enabling it to move based on the state loaded into the memory cell 460.

The reconfigurable stent 100 can be manufactured using various manufacturing technologies including, but not limited to, technology selected from stent manufacturing technology, microelectromechanical systems ("MEMS") manufacturing technology, and a combination of both stent manufacturing technology and MEMS manufacturing technology. In some embodiments, for example, a reconfigurable stent can be manufactured by i) forming at least a portion of the lattice structure of the reconfigurable stent's tubular body using stent manufacturing technology, ii) forming the reconfigurable stent's microcells using MEMS manufacturing technology, and iii) combining the microcells with the lattice structure to form the reconfigurable stent. In such embodiments, at least a portion of the reconfigurable stent's filaments form the lattice structure formed using the stent manufacturing technology. A remaining portion of the filaments can be formed by the microcells, which includes fixing the microcells in a layer to an outside of at least a portion of the filaments formed using the stent manufacturing technology; forming (e.g., monolithically forming) complementary filaments of microcells using the MEMS manufacturing technology; or both fixing the microcells in a layer to an outside of at least a portion of the filaments formed using the stent manufacturing technology and forming complementary filaments of microcells using the MEMS manufacturing technology. However, in some embodiments, a reconfigurable stent can be manufactured primarily by MEMS manufacturing technology.

With respect to stent manufacturing technology, the lattice structure of the reconfigurable stent's tubular body can be formed from small-diameter metallic tubing of stainless steel, a platinum alloy, a cobalt-chromium alloy (e.g., CoCr-NiFeMoMn such as Elgiloy®), a nickel-titanium alloy (e.g. nitinol), or the like. A tube of such tubing is mounted in a laser machining system such that the focal point of the laser impinges upon the surface of the tube. When the laser is applied along with a coaxial jet of gas (e.g., air, oxygen, argon, etc.), the tube is perforated by laser's energy and possibly by chemical reaction with air or oxygen. The tube is moved under the laser along at least two axes, rotational and longitudinal, so that a continuous cut (or kerf) is made while the laser impinges upon the surface of the tube. The laser is also switched on and off under computer control in coordination with the longitudinal and rotational movement so that a discontinuous pattern of cuts is applied to the tube to form at least a portion of the filaments of the reconfigurable stent's lattice structure.

Following the laser-machining process, excessive material is removed from the interior and exterior surfaces of the laser-machined tube, and the tube is further processed in any of a number of further processing steps to produce the reconfigurable stent, which processing steps include fixing the microcells to at least a portion of the filaments formed using the stent manufacturing technology. However, continuing with stent manufacturing technology, a self-expandable stent, for example, can be further processed by successively expanding the laser-machined tube on larger and larger mandrels. At each successive step, the laser-machined tube is subjected to a heat-treatment step to thermally set the tube on an appropriately sized mandrel. For example, a laser-machined tube of a nickel-titanium alloy can be heated at 896° F. (480° C.) for thirty seconds while on the appropriately sized mandrel for the heat-treatment step or expansion stage. Typically, two to six expansion stages are used to fully expand a self-expanding stent of a nickel-titanium alloy. After expansion, the self-expandable stent is finished by a combination of chemical, mechanical, and electrochemical polishing to produce a smooth, biocompatible surface. Microcells can subsequently be fixed to at least a portion of the filaments formed using the stent manufacturing technology. Such a stent can then be chilled to transform it to the soft and deformable martensitic crystalline structure and radially compressed to a size small enough to be placed onto a catheter.

With respect to MEMS manufacturing technology, MEMS manufacturing technology includes micro-machining processes akin to those used to produce integrated circuits but for microcells such as those described in FIGS. 3A-C and 4. Because each microcell of the number of microcells 220 is tens of μm across, tens of thousands or more of the microcells can be generated on a silicon wafer or other substrate of choice.

In further detail, a number of the microcells 220 can be monolithically formed over a respective number of completed memory cells 460 (e.g., CMOS-based SRAM memory cell) for forming a single filament or fixing to a filament manufactured by the stent manufacturing technology. A low-temperature fabrication process for microcell superstructure (e.g., mechanical elements including the microsurface 332, the post 334, the yoke 344, the torsional hinge 346, etc.) can be used to preserve the integrity of metallization forming the underlying CMOS memory cell. The mechanical elements can be sputter-deposited aluminum alloys, another bio-insensitive material, or a combination of these. Sacrificial layers (or spacers) between the mechanical elements can be formed of a deep ultraviolet (DUV)-hardened photoresist. Plasma etching can be used to remove the DUV-hardened photoresist to form air gaps between the mechanical elements such as between the yoke 344 and the stop 354. Whether filaments of the microcells are combined with filaments formed using the stent manufacturing technology or the microcells are fixed in a layer to an outside of the filaments formed using the stent manufacturing technology (or both), such a stent can be subsequently radially compressed to a size small enough to be placed onto a catheter.

The reconfigurable stent 100 can be used, in some embodiments, by mounting a reconfigurable stent on a catheter to form a stent-catheter combination; advancing the stent-catheter combination through a patient's anatomy to provide a treatment; configuring the reconfigurable stent of the stent-catheter combination in accordance with the treatment; disconnecting the reconfigurable stent from the stent-catheter combination; and withdrawing the catheter from the patient.

Mounting the reconfigurable stent on the catheter to form the stent-catheter combination can include connecting (e.g., magnetically connecting) a catheter cable to a reconfigurable stent port.

Advancing the stent-catheter combination through a patient's anatomy to provide a treatment can include advancing the stent-catheter combination to a location in the patient's anatomy including a vessel in need of the treatment. In advancing the stent-catheter combination through a patient's anatomy, the stent-catheter combination can be configured to slide up a low-profile cable rail for deployment at the location in the patient's anatomy including the vessel in need of the treatment.

Configuring the reconfigurable stent of the stent-catheter combination in accordance with the treatment can include, for example, configuring the reconfigurable stent to restore patency to a blocked or partially blocked vessel, reinforce a collapsed vessel, or a combination of these. Combined micromovements of microsurfaces move filaments of the reconfigurable stent to radially expand the stent to provide the treatment. One or more sensors of the reconfigurable stent can be configured to provide sensor data over the catheter cable for moving the microsurfaces in the combined micromovements. Alternatively, or in addition, advanced imaging techniques such as fluoroscopy can be used as an aid for moving the microsurfaces in the combined micromovements. This treatment with the reconfigurable stent, which matches the shape of the vessel, mitigates stress on the vessel compared to conventional stents.

Disconnecting the reconfigurable stent from the stent-catheter combination such as disconnecting the catheter cable from the magnetic port of the reconfigurable stent further includes completely detaching the catheter from the reconfigurable stent after the shape of the reconfigurable stent is matched to the vessel.

Withdrawing the catheter from the patient includes completely removing the catheter from the patient.

The reconfigurable stent 100 can be further used, in some embodiments, by advancing the catheter through the patient's anatomy to provide further treatment; connecting the catheter to the reconfigurable stent to form the stent-catheter combination; configuring the reconfigurable stent of the stent-catheter combination in accordance with the further treatment; disconnecting the reconfigurable stent from the stent-catheter combination; and withdrawing the catheter from the patient.

Connecting the catheter to the reconfigurable stent to form the stent-catheter combination includes finding the magnetic port of the reconfigurable stent with the catheter and connecting the catheter cable to the magnetic port of the reconfigurable stent.

Configuring the reconfigurable stent of the stent-catheter combination in accordance with the further treatment can include, for example, configuring the reconfigurable stent to restore patency to a vessel lost since a previous treatment. Combined micromovements of the microsurfaces move the filaments of the reconfigurable stent to radially expand the stent to provide the treatment. One or more sensors of the reconfigurable stent can be configured to provide sensor data over the catheter cable for moving the microsurfaces. Advanced imaging techniques such as fluoroscopy can be used as an aid for moving the microsurfaces in the combined micromovements. The treatment with the reconfigurable stent, which matches the shape of the vessel, mitigates stress on the vessel compared to conventional stents.

Again, disconnecting the reconfigurable stent from the stent-catheter combination such as disconnecting the catheter cable from the magnetic port of the reconfigurable stent further includes completely detaching the catheter from the reconfigurable stent after the shape of the reconfigurable stent is matched to the vessel. Withdrawing the catheter from the patient's anatomy includes completely removing the catheter from the patient's anatomy.

This process can be repeated every few months to make sure the reconfigurable stent can mitigate, for example, any re-buildup of plaque or thrombus in the same region of the vessel.

In some embodiments, the reconfigurable stent can be controlled even post deployment to re-adjust without any need of access into the vessel such as by communicating with the deployed reconfigurable stent in a vessel and having the number of filaments acquire a reconfigured form and orientation.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. A device, comprising:
    a tubular body including a lattice structure, the tubular body adapted for an anatomical vessel lumen;
    a plurality of filaments forming at least a portion of the lattice structure; and
    a plurality of microcells forming at least a portion of the plurality of filaments, wherein:
        each microcell of the plurality of microcells is configured with a movable microsurface,
        each microcell of the plurality of microcells includes the movable microsurface mounted on a torsional hinge over at least a pair of electrodes configured to electrostatically hold in place at least one corner of the movable microsurface, and
        combined micromovements of movable microsurfaces shape the tubular body to the anatomical vessel lumen.

2. The device according to claim 1, wherein the plurality of microcells forming at least the portion of the plurality of filaments are arranged in one or more programmatically addressable rows along respective filaments.

3. The device according to claim 1, wherein each microcell of the plurality of microcells further includes a memory cell configured to store state data for at least one electrode of the pair of electrodes to electrostatically hold in place the at least one corner of the movable microsurface.

4. The device according to claim 1, further comprising a polymeric casing disposed around the tubular body, the polymeric casing configured to protect the plurality of filaments from corrosion.

5. The device according to claim 4, wherein the polymeric casing is further configured to accept tissue ingrowth.

6. The device according to claim 1, further comprising a plurality of sensors associated with each filament of the plurality of filaments, each sensor of the plurality of sensors configured to provide sensor data for moving the movable microsurfaces.

7. The device according to claim 1, further comprising a port configured to connect with a cable, the port configured to accept power and control signals for moving the movable microsurfaces.

8. A stent, comprising:
a plurality of filaments arranged to form a tubular body of the stent;
a plurality of programmatically addressable microcells forming each filament of the plurality of filaments; and
a plurality of movable microsurfaces, each microsurface of the plurality of movable microsurfaces configured to tilt a first microsurface corner toward a blood vessel wall and a second microsurface corner away from the blood vessel wall, wherein the plurality of programmatically addressable microcells is configured to move the movable microsurfaces thereof to match the blood vessel wall, thereby maintaining patency while mitigating stress on the blood vessel wall.

9. The stent according to claim 8, wherein each microsurface of the plurality of movable microsurfaces is mounted on a torsional hinge over at least a pair of electrodes configured to electrostatically hold in place at least one corner of the microsurface.

10. The stent according to claim 8, further comprising a polymeric casing disposed about the tubular body of the stent, the polymeric casing configured to protect the plurality of filaments from corrosion and accept tissue ingrowth.

11. The stent according to claim 8, further comprising a plurality of sensors disposed along each filament of the plurality of filaments, each sensor of the plurality of sensors configured to provide sensor data for moving the movable microsurfaces.

12. The stent according to claim 8, further comprising a port configured to connect with a cable, the port configured to accept power and control signals for moving the movable microsurfaces.

13. A system, comprising:
a) a stent including:
a plurality of filaments arranged to form at least a portion of a tubular body of the stent;
a plurality of microcells forming at least a portion of the plurality of filaments, wherein each microcell of the plurality of microcells includes a moveable microsurface; and
a port configured to accept power and control signals for moving the movable microsurfaces; and
b) a catheter including a cable configured to connect with the port and provide the power and the control signals for moving the movable microsurfaces, wherein moving the movable microsurfaces includes matching a shape of a vessel.

14. The system according to claim 13, wherein the stent further includes a polymeric casing disposed around the tubular body, the polymeric casing configured to protect the plurality of filaments from corrosion and accept tissue ingrowth.

15. The system according to claim 13, wherein the port is a magnetic port configured to facilitate reconnecting the cable with the port when the stent is disposed in vivo.

16. The system according to claim 13, wherein the stent further includes a plurality of sensors disposed along each filament of the plurality of filaments, each sensor of the plurality of sensors configured to provide sensor data over the cable for moving the movable microsurfaces.

17. The system according to claim 16, wherein the catheter further includes a microcontroller including a shape-determining algorithm configured for matching the shape of the vessel from the sensor data.

18. The system according to claim 13, wherein each microcell of the plurality of microcells is configured to tilt a first microsurface corner toward a wall of the vessel and a second microsurface corner away from the wall of the vessel.

19. The system according to claim 13, wherein each microcell of the plurality of microcells is mounted on a torsional hinge over at least a pair of electrodes configured to electrostatically hold in place at least one corner of the movable microsurface.

20. A device, comprising:
a tubular body including a lattice structure, the tubular body adapted for an anatomical vessel lumen;
a plurality of filaments forming at least a portion of the lattice structure; and
a plurality of microcells forming at least a portion of the plurality of filaments, wherein:
each microcell of the plurality of microcells is configured with a movable microsurface, and
combined micromovements of movable microsurfaces shape the tubular body to the anatomical vessel lumen; and
a port configured to connect with a cable, the port configured to accept power and control signals for moving the movable microsurfaces.

21. The device according to claim 20, wherein the plurality of microcells forming at least the portion of the plurality of filaments are arranged in one or more programmatically addressable rows along respective filaments.

22. The device according to claim 20, wherein each microcell of the plurality of microcells includes the movable microsurface mounted on a torsional hinge over at least a pair of electrodes configured to electrostatically hold in place at least one corner of the movable microsurface.

23. The device according to claim 22, wherein each microcell of the plurality of microcells further includes a memory cell configured to store state data for at least one electrode of the pair of electrodes to electrostatically hold in place the at least one corner of the movable microsurface.

24. The device according to claim 20, further comprising a plurality of sensors associated with each filament of the plurality of filaments, each sensor of the plurality of sensors configured to provide sensor data for moving the movable microsurfaces.

* * * * *